(12) United States Patent
Jessell et al.

(10) Patent No.: US 7,393,686 B1
(45) Date of Patent: Jul. 1, 2008

(54) GENETIC DEMONSTRATION OF REQUIREMENT FOR NKX6.1 AND NKX2.2 IN VENTRAL NEURON GENERATION

(75) Inventors: Thomas M. Jessell, Bronx, NY (US); James Briscoe, London (GB); Johan Ericson, Hasselby (SE); John L. R. Rubenstein, San Francisco, CA (US); Maike Sander, Hamburg (DE)

(73) Assignees: Trustees of Columbia University in the City of New York, New York, NY (US); The Regents of the University of California, Oakland, CA (US)

( * ) Notice: Subject to any disclaimer, the term of this patent is extended or adjusted under 35 U.S.C. 154(b) by 123 days.

(21) Appl. No.: 09/654,462

(22) Filed: Sep. 1, 2000

Related U.S. Application Data

(63) Continuation-in-part of application No. 09/569,259, filed on May 11, 2000.

(51) Int. Cl.
*C12N 5/00* (2006.01)
*C12N 5/02* (2006.01)
*C12N 15/00* (2006.01)

(52) U.S. Cl. ..................... 435/377; 435/455

(58) Field of Classification Search ............... 435/325, 435/377, 455
See application file for complete search history.

(56) References Cited

U.S. PATENT DOCUMENTS

| | | | |
|---|---|---|---|
| 6,235,885 B1 | 5/2001 | Jessell et al. | |
| 6,387,656 B1 | 5/2002 | Jessell et al. | |
| 6,566,092 B1 | 5/2003 | Jessell et al. | |
| 6,955,802 B1 * | 10/2005 | Jessell et al. | 424/9.2 |
| 2002/0197678 A1 | 12/2002 | Jessell et al. | |
| 2003/0104374 A1 | 6/2003 | Jessell et al. | |
| 2004/0005602 A1 | 1/2004 | Jessell et al. | |

FOREIGN PATENT DOCUMENTS

| | | |
|---|---|---|
| WO | WO 95/23223 A1 | 8/1995 |
| WO | WO 99/00516 A2 | 1/1999 |
| WO | WO00/09676 A2 | 2/2000 |
| WO | WO 00/18884 A1 | 4/2000 |
| WO | WO 0184933 | 11/2001 |
| WO | WO 0218545 | 3/2002 |

OTHER PUBLICATIONS

Stem Cells: Scientific Progress and Future Research Directions. Chapters 1 and 2, pp. 1-9. Department of Health and Human Services. Jun. 2001. http://www.nih.gov/news/stemcell/scireport.htm.*
Friedmann, T. Overcoming the obstacles to gene therapy. Sci. Am. Jun. 1997, pp. 96-101.*
Orkin and Motulsky (1995) Report and recommendations of the panel to assess the NIH investment in research on gene therapy.*
Verma et al. (1997) Gene therapy—promises, problems and prospects. Nature 389: 239-242.*
Briscoe et al. (2000) "A Homeodomain Protein Code Specifies Progenitor Cell Identity And Neuronal Fate In The Ventral Neural Tube" *Cell* 101:435-445.
Mirmira et al. (2000) "Beta-Cell Differentiation Factor Nkx6.1 Container Distinct DNA Binding Interference And Transcriptional Repression Domains" *J. Biol. Chem.* 275(19):14743-114751 (Exhibit 1).
Oster et al. (1998) "Homeobox Gene Product Nkx 6.1 Immunoreactivity In Nuclei Of Endocrine Cells Of Rat And Mouse Stomach" *J. Histochem. And Cytochem.* 46(6):717-721 (Exhibit 2); and.
Schwitzgebel et al. (2000) "Expression Of Neurogenin3 Reveals An Islet Cell Precursor Population In The Pancreas" *Genes & Development* 14(17):2134-2139 (Exhibit 3).
Anderson. S.A. et al., (1997) "Interneuron Migration from Basal Forebrain to Neocortex: Dependence on DLx Genes" *Science* 278:474-476 (Exhibit 1).
Arber, S. et al., (1999) "Requirement for the Homeobox Gene Hb9 in the Consolidation of Motor Neuron Identity" *Neuron* 23:659-674 (Exhibit 2).
Briscoe, J. et al., (1999) "Homeobox gene Nkx2.2 and specification of neuronal identity by graded Sonic Hedgehog signalling" *Nature* 398:622-627 (Exhibit 3).
Briscoe, J. et al., (2000) "A Homeodomain Protein Code Specifies Progenitor Cell Identity and Neuronal Fate in the Ventral Tube" *Cell* 101:435-445 (Exhibit 4).
Burrill, J.D. et al., (1997) "PAX2 is expressed in multiple spinal cord interneurons, including a population on EN1 interneurons that require PAX6 for their development" *Development* 124:4493-4503 (Exhibit 5).
Chu, H. et al., (1998) "Formation and specification of ventral neuroblasts is controlled by vnd in Drosophila neurogenesis" *Genes & Dev.* 12:3613-3624 (Exhibit 6).
Ericson, J. et al., (1997) "Graded Sonic Hedgehog Signaling and the Specification of Cell Fate in the Ventral Neutral Tube" *Cold Spring Harb. Symp. Quant. Biol.* 62:451-466 (Exhibit 7).
Ericson, J. et al., (1996) "Two Critical Periods of Sonic Hedgehog Signaling Required for the Specification of Motor Neuron Identity" *Cell* 87:661-673 (Exhibit 8).

(Continued)

*Primary Examiner*—Anne-Marie Falk
(74) *Attorney, Agent, or Firm*—John P. White; Cooper & Dunham LLP

(57) ABSTRACT

This invention provides a method of converting a stem cell into a ventral neuron which comprises introducing into the stem cell a nucleic acid which expresses homeodomain transcription factor Nkx6.1 protein in the stem cell so as to thereby convert the stem cell into the ventral neuron. Provided are methods of diagnosing a motor neuron degenerative disease in a subject. Also provides is a method of treating neuronal degeneration in a subject which comprises implanting in diseased neural tissue of the subject a neural stem cell which comprises an isolated nucleic acid molecule which is capable of expressing homeodomain Nkx6.1 protein under conditions such that the stem cell is converted into a motor neuron after implantation, thereby treating neuronal degeneration in the subject.

2 Claims, 9 Drawing Sheets

OTHER PUBLICATIONS

Ericson, J. et al., (1997) "Pax6 Controls Progenitor Cell Identity and Neuronal Fate in Response to Graded Shh Signaling" *Cell* 90:169-180 (Exhibit 9).

Goulding, M.D. et al., (1991) "Pax-3, a novel murine DNA binding protein expressed during early neurogenesis" *EMBO J.* 10:1135-47 (Exhibit 10).

Hammerschmidt, M. et al., (1997) "The world according to hedgehog" *Trends Genet.* 13:14-21 (Exhibit 11).

Hebrok, M. et al., (1998) "Notochord repression of endodermal Sonic hedgehog permits pancreas development" *Genes & Dev.* 12:1705-1713 (Exhibit 12).

Inoue, H. et al., (1997) "Isolation, characterization, and chromosomal mapping of the human Nkx6.1 gene (NKX6A), a new pancreatic islet homeobox gene" *Genomics* 40:367-370][ (Exhibit 13).

Lumsden, A. et al., (1996) "Patterning the Vertebrate Neuraxis" R. *Science* 274: 1109-1114 (Exhibit 14).

Matise, M.P. et al., (1997) "Expression Patterns of Development Control Genes in Normal and Engrailed-1 Mutant Mouse Spinal Cord Reveal Early Diversity in Developing Interneurons" *J. Neurosci.* 17:7805-7816 (Exhibit 15).

McDonald, J. A. et al., (1998) "Dorsoventral patterning in the Drosophila central nervous system: the vnd homeobox gene specifies ventral column identity" *Genes & Dev.* 12:3603-3612 (Exhibit 16).

Pabst, O. et al., (1998) "Nkx2-9 is novel homeobox transcription factor which demarcates ventral domains in the developing mouse CNS" *Mech. Dev.* 73: 85-93 (Exhibit 17).

Pattyn, A. et al., (1997) "Expression and interactions of the two closely related homeobox genes Phox2a and Phox2b during neurogensis" *Development* 124:4065-4075 (Exhibit 18).

Pierani, A. et al., (1999) "A Sonic Hedgehog-Independent, Retinoid-Activated Pathway of Neurogenesis in the Ventral Spinal Cord" *Cell* 97:903-915 (Exhibit 19).

Qiu, M. et al., (1998) "Control of anteroposterior and dorsoventral domains of Nkx-6.1 gene expression relative to other Nkx genes during vertebrate CNS development" *Mech. Dev.* 72:77-88 (Exhibit 20).

Rubenstein, J.L. et al., (1998) "Patterning of the embryonic forebrain" *Curr. Opin. Neurobiol.* 8:18-26 (Exhibit 21).

Rubenstein, J.L. et al., (1998) "Regionalization of the Prosencephalic Neural Plate" *Annu. Rev. Neurosci.* 21:445-477 (Exhibit 22).

Sussel, L. et al., (1999) "Loss of Nkx2.1 homeobox gene function results in a ventral to dorsal molecular respecification within the basal telencephalon: evidence for a transformation of the pallidum into the striatum" *Development* 126:3359-3370 (Exhibit 23).

Tanabe, Y. et al., (1996) "Diversity and Pattern in the Developing Spinal Cord" *Science* 274:1115-23 (Exhibit 24).

Thaler, J. et al., (1999) "Active Suppression of Interneuron Programs within Developing Motor Neurons Revealed by Analysis of Homeodomain Factor HB9" *Neuron* 23:675-678 (Exhibit 25).

Tsuchida, T. et al., (1994) "Topographic Organization of Embryonic Motor Neurons Defined by Expression of LIM Homeobox Genes" *Cell* 79:957-970 (Exhibit 26).

Valerius, M. T. et al., (1995) "Gsh-1: A Novel Murine Homeobox Gene Expressed in the Central Nervous System" *Dev. Dyn.* 203:337-51 (Exhibit 27) and.

Weiss, J. B. et al., (1998) "Dorsoventral pattering in the Drosophila central nervous system: the intermediate neuroblasts defective homeobox gene specifies intermediate column identity" *Genes & Dev*, 12:3591-3602 (Exhibit 28).

U.S. Appl. No. 09/569,259, filed May 11, 2000 on behalf of Thomas M. Jessell et al., including pending claims (Exhibit 1).

U.S. Appl. No. 10/362,437, filed Feb. 20, 2003 on behalf of Thomas M. Jessell et al., including pending claims (Exhibit 2).

European Patent Application No. 01968382, filed Aug. 31, 2001, European Publication No. EP1315794, published Jun. 4, 2003 on behalf of The Trustees of Columbia University in the City of New York, including Voluntary Amendment filed Mar. 28, 2003 (Exhibit 5).

Campbell, G. et al., (1999) "Transducing the Dpp Morphogen Gradient in the Wing of Drosophila: Regulation of Dpp Targets by brinker", *Cell* 96: 553-562 (Exhibit 6).

Chiang, C. et al., (1996) "Cyclopia and Defective Axial Patterning in Mice Lacking Sonic Hedgehog Gene Function", *Nature* 383: 407-413 (Exhibit 7).

Dasen, J.S. et al., (1999) "Combinatorial Codes in Signaling and Synergy: Lessons From Pituitary Development", *Curr. Opin. Genet. & Dev.* 9: 566-574 (Exhibit 8).

Ding, Q. et al., (1998) "Diminished Sonic Hedgehog Signaling and Lack of Floor Plate Differentiation in Gli2 Mutant Mice", *Development* 125: 2533-2543 (Exhibit 9).

Doetsch, F. et al., (1999) "Subventricular Zone Astrocytes Are Neural Stem Cells in the Adult Mammalian Brain", *Cell* 97:703-716 (Exhibit 10).

Erskine, L. et al. (1998) "Progenitor Dispersal and the Origin of Early Neuronal Phenotypes in the Chick Embryo Spinal Cord" *Dev. Biol.* 199: 26-41 (Exhibit 11).

Funayama, N. et al. (1999) "Coelom Formation: Binary Decision of the Lateral Plate Mesoderm is Controlled by the Ectoderm" *Development* 126: 4129-4138 (Exhibit 12).

Gage, F.H. (2000) "Mammalian Neural Stem Cells", *Science* 287:1433-1438 (Exhibit 13).

Huang, A.M. et al. (1997) "An Anteroposterior Dorsal Gradient in the Drosophila Embryo", *Genes & Dev.* 11: 1963-1973 (Exhibit 14).

Ingham, P.W. (1998) "Transducing Hedgehog: The Story So Far" *EMBO J.* 17:3505-3511 (Exhibit 15).

Jazwinska, A. et al. (1999) "The Drosophila Gene brinker Reveals a Novel Mechanism of Dpp Target Gene Regulation", *Cell* 96: 563-573 (Exhibit 16).

Johansson, C.B. et al. (1999) "Identification of a Neural Stem Cell in the Adult Mammalian Central Nervous System", *Cell* 96: 25-34 (Exhibit 17).

Kraut, R. et al. (1991) "Spatial Regulation of the Gap Gene giant During Drosophila Development", *Development* 111: 601-609 (Exhibit 18).

Krishnan, V. et al. (1997) "Mediation of Sonic Hedgehog-Induced Expression of COUP-TFII by a Protein Phosphatase", *Science* 278: 1947-1950 (Exhibit 19).

Lawrence, P.A. et al. (1996) "Morphogens, Compartments, and Pattern: Lessons from Drosophila?", *Cell* 85: 951-961 (Exhibit 20).

Lewis, K.E. et al. (1999) "Expression of ptc and gli Genes in talpid[3] Suggests Bifurcation in Shh Pathway" *Development* 126: 2397-2407 (Exhibit 21).

Mansouri, A. et al. (1998) "Pax3 and Pax7 are Expressed in Commissural Neurons and Restrict Ventral Neuronal Identity in the Spinal Cord", *Mech. Dev.* 78: 171-178 (Exhibit 22).

Marti, E. et al. (1995) "Distribution of Sonic Hedgehog Peptides in the Developing Chick and Mouse Embryo", *Development* 121: 2537-2547 (Exhibit 23).

Matise, M.P. et al. (1998) "Gli2 is Required for Induction of Floor Plate and Adjacent Cells, But Not Most Ventral Neurons in the Mouse Central Nervous System", *Development* 125: 2759-2770 (Exhibit 24).

McDowell, N. et al. (1999) "Activin as a Morphogen in *Xenopus mesoderm* Induction", *Semin. Cell & Dev. Biol.* 10: 311-317 (Exhibit 25).

Minami, M. et al. (1999) "Brinker is a Target of Dpp in *Drosophila* that Negatively Regulates Dpp-dependent Genes", *Nature* 398: 242-246 (Exhibit 26).

Papin, C. et al. (2000) "Gradual Refinement of Activin-Induced Thresholds Requires Protein Synthesis" *Dev. Biol.* 217: 166-172 (Exhibit 27).

Pierani, A. et al. (1999) "A Sonic Hedgehog-Independent, Retinoid-Activated Pathway of Neurogenesis in the Ventral Spinal Cord", *Cell* 97: 903-915 (Exhibit 28).

Roelink, H. et al. (1995) "Floor Plate and Motor Neuron Induction by Different Concentrations of the Amino-Terminal Cleavage Product of Sonic Hedgehog Autoproteolysis", *Cell* 81: 445-455 (Exhibit 29).

Rowitch, D.H. et al. (1999) "Sonic hedgehog Regulates Proliferation and Inhibits Differentiation of CNS Precursor Cells", *J. Neurosci.* 19: 8954-8965 (Exhibit 30).

Ruiz i Altaba, A. (1999) "Gli Proteins and Hedgehog Signaling: Development and Cancer", *Trends Genet.* 15: 418-425 (Exhibit 31).

Sharma, K. et al. (1998) "LIM Homedomain Factors Lhx3 and Lhx4 Assign Subtype Identities for Motor Neurons", *Cell* 95: 817-828 (Exhibit 32).

Smith, J.C. (1995) "Mesoderm-Inducing Factors and Mesodermal Patterning", *Curr. Opin. Cell Biol.* 7: 856-861 (Exhibit 33).

Tanabe, Y. et al. (1998) "Specification of Motor Neuron Identity by the MNR2 Homeodomain Protein", Cell 95: 67-80 (Exhibit 34).

Wu, X. et al. (1998) "Two Distinct Mechanisms for Differential Positioning of Gene Expression Borders Involving the *Drosophila* Gap Protein Giant", *Development* 125: 3765-3774 (Exhibit 35).

Horner et al. (2000) "Regenerating the Damaged Central Nervous System", 407: 963-970.

Jackowski (1995) "Neural Injury Repair" pp. 303-317.

Hamburger,V. et al. (1951) "A Series Of Normal Stages In The Development Of The Chick Embryo", *J. Morphol.* 88: 49-92.

Langman, J. et al. (1966) "Behavior of Neuroepithelial Cells During Closure Of The Neural Tube", *J. Comp. Neur.* 127: 399-411.

Leber, S.M. et al. (1995) "Migratory Paths Of Neurons And Glia In The Embryonic Chick Spinal Cord", *J. Neurosci.* 15: 1236-1248.

Muramatsu, T. et al. (1997) "Comparison Of Three Nonviral Transfection Methods For Foreign Gene Expression In Early Chicken Embryons In Ovo", *Biochem. Biophys. Res. Commun.* 230: 376-380.

Sander, M. et al. (2000) "Ventral Neural Patterning By Nkx Homeobox Genes: Nkx6.1 Controls Somatic Motor Neuron And Ventral Interneuron Fates", *Genes & Development* 14(17): 2134-2139.

Struhl, G. et al. (1992) "Control Of *Drosophila* Body Pattern By The hunchback Morphogen Gradient", *Cell* 69: 237-249.

Yamada, T. et al. (1993) "Control Of Cell Pattern In The Neural Tube: Motor Neuron Induction By Diffusible Factors From Notochord And Floor Plate", *Cell* 73: 673-686.

Basler, K. et al. (1993) "Control of cell pattern in the neural tube: Regulation of cell differentiation by dorsalin-1, a novel TGF beta family member", *Cell* 73: 687-702 (Exhibit 36).

Briscoe, J., and Ericson, J. (2001) "Specification of neuronal fates in the ventral neural tube", *Curr. Opin. Neurobiol.* 11: 43-49 (Exhibit 37).

Briscoe, J. et al. (2001) "A hedgehog-insensitive form of patched provides evidence for direct long-range patterning activity of Sonic hedgehog in the neural tube", *Molecular Cell* 7: 1279-1291 (Exhibit 38).

Cai, J. et al. (1999) "Expression and regulation of the chicken Nkx-6.2 homeobox gene suggest its possible involvement in the ventral neural patterning and cell fate specification", *Dev. Dyn.* 216: 459-468 (Exhibit 39).

Davis, C.A. et al. (1991) "Examining pattern formation in mouse, chicken and frog embryos with an En-specific antiserum", *Development* 111: 287-298 (Exhibit 40).

Eberhard, D. et al. (2000) "Transcriptional repression by Pax5 (BSAP) through interaction with corepressors of the Groucho family"*EMBO J.* 19: 2292-2303 (Exhibit 41).

Hoshiyama, D. et al. (1998) "Sponge Pax cDNA related to Pax-2/5/8 and ancient gene duplications in the Pax family", *J. Mol. Evol.* 47: 640-648 (Exhibit 42).

Jörgensen, M.C. et al. (1999) "Cloning and DNA-binding properties of the rat pancreatic beta-cell-specific factor Nkx6.1", *FEBS Lett.* 461: 287-294 (Exhibit 43).

Kraut, R. and Levine, M. (1991) "Mutually repressive interactions between the gap genes giant and Kruppel define middle body regions of the *Drosophila* embryo" *Development* 111: 611-621 (Exhibit 44).

Komuro, I. et al. (1993) "Gtx: a novel murine homeobox-containing gene, expressed specifically in glial cells of the brain and germ cells of testis, has a transcriptional repressor activity in vitro for a serum-inducible promoter" *EMBO* 12: 1387-1401 (Exhibit 45).

Lee, S. et al. (2001) "Cloning, expression and chromosomal location of NKX6B to 10q26, a region frequently deleted in brain tumors", *Mammalian Genome* 12: 157-162 (Exhibit 46).

Mombaerts, P. et al. (1996) "Visualizing an olfactory sensory map", *Cell* 87: 675-686 (Exhibit 47).

Moran-Rivard, L. et al. (2001) "Evx1 is a postmitotic determinant of V0 interneuron identity in the spinal cord", *Neuron* 29: 385-399 (Exhibit 48).

Muhr, J. et al. (2001) "Groucho-mediated transcriptional repression establishes progenitor cell pattern and neuronal fate in the ventral neural tube", *Cell* 104: 861-873 (Exhibit 49).

Novitch, B. et al. (2001) "Coordinate regulation of motor neuron subtype identity and pan-neural properties by the bHLH repressor Olig2", *Neuron* 31: 773-789 (Exhibit 50).

Nutt, S.L. et al. (1999) "Commitment to the B-lymphoid lineage depends on the transcription factor Pax5", *Nature* 401: 556-562 (Exhibit 51).

Pabst, O. et al. (2000) "NKX2 gene expression in neuroectoderm but not in mesendodermally derived structures depends on sonic hedgehog in mouse embryos", *Dev. Genes. Evol.* 210: 47-50 (Exhibit 52).

Peters, T. et al. (2000) "Organization of mouse Iroquois homeobox genes in two clusters suggests a conserved regulation and function in vertebrate development", *Genome Res.* 10: 1453-62 (Exhibit 53).

Pierani, A. et al. (2001) "Control of interneuron fate in the developing spinal cord by the progenitor homeodomain protein Dbx1" *Neuron* 29: 367-384 (Exhibit 54).

Rolink, A.G. et al. (1999) "Long-term in vivo reconstitution of T-cell development by Pax5-deficient B-cell progenitors", *Nature* 401: 603-606 (Exhibit 55).

Schaeren-Wiemers, N. and Gerfin-Moser, A. (1993) "A single protocol to detect transcripts of various types and expression levels in neural tissue and cultured cells: in situ hybridization using digoxigenin-labeld cRNA probes", *Histochemistry* 100: 431-440 (Exhibit 56).

Shoji, H. et al. (1996) "Regionalized expression of the Dbx family homeobox genes in the embryonic CNS of the mouse", *Mech. Dev.* 56: 25-39 (Exhibit 57).

Stanojevic, D., Small, S. and Levine, M. (1991) "Regulation of a segmentation stripe by overlapping activators and repressors in the *Drosophila* embryo", *Science* 254: 1385-1387 (Exhibit 58).

Tanaka, M., Yamasaki, N., Izumo, S. (2000) "Phenotypic characterization of the murine Nkx2.6 homeobox gene by gene targeting", *Mol. Cell. Biol.* 20: 2874-2879 (Exhibit 59).

Toresson, H., Potter, S.S. and Campbell, K. (2000) "Genetic control of dorsal-ventral identity in the telencephalon: opposing roles for Pax6 and Gsh2", *Development* 127: 4361-4371 (Exhibit 60).

Wang, C.C. et al. (2000) "Conserved linkage of NK-2 homeobox gene pairs Nkx2-2/2-4 and NK-2-1/2-9 in mammals", *Mamm. Genome* 11: 466-468 (Exhibit 61).

Yun, K., Potter, S. and Rubenstein, J.L. (2001) "Gsh2 and Pax6 play complementary roles in dorsoventral patterning of the mammalian telencephalon", *Development* 128: 193-205 (Exhibit 62); and.

Canadian Patent Application No. 2,419,851, filed Aug. 31, 2001, on behalf of The Trustees of Columbia University in the City of New York, including a copy of Aug. 25, 2003 Voluntary Amendment (Exhibit 63).

Sander et al. (2000) "Ventral Neural Patterning by Nkx homeobox genes: Nkx6.1 Controls Somatic Motor Neuron and Ventral Interneuron Fates," *Genes & Development* 14: 2134-2139.

Cai, J. et al. (2001) "Mice lacking the *Nkx6.2* (*Gtx*) homeodomain transcription factor develop and reproduce normally," *Molecular and Cellular Biology* 21: 4399-4403.

Palmer, T.D. et al. (1999) "Fibroblast growth factor-2 activates a latent neurogenic program in neural stem cells from diverse regions of the adult CNS," *The Journal of Neuroscience* 19: 8487-8497.

* cited by examiner

Figure 6

```
  1 mlavgamegt rqsafllssp plaalhsmae mktplypaay pplpagppss sssssssssp
 61 spplgthnpg glkppatggl sslgsppqql saatphginn ilsrpsmpva sgaalpsasp
121 sgsssssss asassasaaa aaaaaaaaaa sspagllagl prfsslsppp pppglyfsps
181 aaavaavgry pkplaelpgr tpifwpgvmq sppwrdarla ctphqgsill dkdgkrkhtr
241 ptfsgqqifa lektfeqtky lagperarla yslgmtesqv kvwfqnrrtk wrkkhaaema
301 takkkqdset erlkgasene eedddynkpl dpnsddekit qllkkhksss ggggglllha
361 sepesss
```

Figure 7

```
  1 cgtgggatgt tagcggtggg ggcaatggag ggcacccggc agagcgcatt cctgctcagc
 61 agccctcccc tggccgccct gcacagcatg gccgagatga agacccccgct gtaccctgcc
121 gcgtatcccc cgctgcctgc cggcccccccc tcctcctcgt cctcgtcgtc gtcctcctcg
181 tcgccctccc cgcctctggg cacccacaac ccaggcggcc tgaagccccc ggccacgggg
241 gggctctcat ccctcggcag ccccccgcag cagctctcgg ccgccacccc acacggcatc
301 aacaatatcc tgagccggcc ctccatgccc gtggcctcgg gggccgccct gccctccgcc
361 tcgccctccg gttcctcctc ctcctcttcc tcgtccgcct ctgcctcctc cgcctctgcc
421 gccgccgcgg ctgctgccgc ggccgcagcc gccgcctcat ccccggcggg gctgctggcc
481 ggactgccac gctttagcag cctgagcccg ccgccgccgc cgcccgggct ctacttcagc
541 cccagcgccg cggccgtggc cgccgtgggc cggtacccca agccgctggc tgagctgcct
601 ggccggacgc ccatcttctg gcccggagtg atgcagagcc cgccctggag ggacgcacgc
661 ctggcctgta ccccctcgtga gt
```

Figure 8

```
  1 tcacagatca aggatccatt ttgttggaca aagacgggaa gagaaaacac acgagaccca
 61 cttttccgg acagcagatc ttcgccctgg agaagacttt cgaacaaaca aaatacttgg
121 cggggcccga gagggctcgt ttggcctatt cgttggggat gacagagagt caggtcaagg
181 tgagt
```

Figure 9

```
  1 cctcaggtct ggttccagaa ccgccggacc aagtggagga agaagcacgc tgccgagatg
 61 gccacggcca agaagaagca ggactcggag acagagcgcc tcaaggggc  ctcggagaac
121 gaggaagagg acgacgacta caataagcct ctggatccca actcggacga cgagaaaatc
181 acgcagctgt tgaagaagca caagtccagc agcggcggcg gcggcggcct cctactgcac
241 gcgtccgagc cggayayctc atcctgaacg ccg
```

GENETIC DEMONSTRATION OF REQUIREMENT FOR NKX6.1 AND NKX2.2 IN VENTRAL NEURON GENERATION

This application is a continuation-in-part of U.S. Ser. No. 09/569,259, filed May 11, 2000, still pending, the contents of which are hereby incorporated by reference into the present application.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

The invention described herein was made with government support under NIH Grants DA12462, DK21344 and DK41822. Accordingly, the United States government has certain rights in this invention.

BACKGROUND OF THE INVENTION

During the development of the embryonic central nervous system (CNS) the mechanisms that specify regional identity and neuronal fate are intimately linked (Anderson et al. 1997; Lumsden and Krumlauf 1996; Rubenstein et al. 1998). In the ventral half of the CNS, for example, the secreted factor Sonic hedgehog (Shh) has a fundamental role in controlling both regional pattern and neuronal fate (Tanabe and Jessell 1996; Ericson et al. 19976; Hammerschmidth et al. 1997). Shh appears to function as a gradient signal. In the spinal cord, five distinct classes of neurons can be generated in vitro in response to two- to threefold changes in the concentration of Shh, and the position at which each neuronal class is generated in vivo is predicted by the concentration required for their induction in vivo (Ericson et al. 1997a; Briscoe et al. 2000). Thus, neurons generated in more ventral regions of the neural tube require progressively higher concentrations of Shh for their induction.

The genetic programs activated in neural progenitor cells in response to Shh signaling, however, remain incompletely defined. Emerging evidence suggests that homeobox genes function as critical intermediaries in the neural response to Shh signals (Lumsden and Krumlauf 1996; Tanabe and Jessell 1996; Ericson et al. 1997; Hammerschmidth et al. 1997; Rubenstein et al. 1998). Several homeobox genes are expressed by ventral progenitor cells, and their expression is regulated by Shh. Gain-of-function studies on homeobox gene action in the chick neural tube have provided evidence that homeodomain proteins are critical for the interpretation of graded Shh signaling and that they function to delineate progenitor domains and control neuronal subtype identity (Briscoe et al. 2000). Consistent with these findings, the pattern of generation of neuronal subtypes in the basal telencephalon and in the ventral-most region of the spinal cord is perturbed in mice carrying mutations in certain Shh-regulated homeobox genes (Ericson et al. 1997; Sussel et al. 1999; Pierani et al., unpublished).

Members of the Nkx class of homeobox genes are expressed by progenitor cells along the entire rostro-caudal axis of the ventral neural tube, and their expression is dependent on Shh signaling (Rubenstein and Beachy 1998). Mutation in the Nkx2.1 or Nkx2.2 genes leads to defects in ventral neural patterning (Briscoe et al. 1999; Sussel et al. 1999), raising the possibility that Nkx genes play a key role in the control of ventral patterning in the ventral region of the CNS. Genetic studies to assess the role of Nkx genes have, however, focused on only the most ventral region of the neural tube. A recently identified Nkx gene, Nkx6.1, is expressed more widely by most progenitor cells within the ventral neural tube (Pabst et al. 1998; Qiu et al. 1998; Briscoe et al. 1999), suggesting that it may have a prominent role in ventral neural patterning. Here experiments show that in mouse embryos Nkx6.1 is expressed by ventral progenitors that give rise to motor (MN), V2, and V3 neurons. Mice carrying a null mutation of Nkx6.1 exhibit a ventral-to-dorsal switch in the identity of progenitor cells and a corresponding switch in the identity of the neuronal subtype that emerges from the ventral neural tube. The generation of MN and V2 neurons is markedly reduced, and there is a ventral expansion in the generation of a more dorsal V1 neuronal subtype. Together, these findings indicate that Nkx6.1 has a critical role in the specification of MN and V2 neuron subtype identity and, more generally, that Nkx genes play a role in the interpretation of graded Shh signaling.

SUMMARY OF THE INVENTION

This invention provides a method of converting a stem cell into a ventral neuron which comprises introducing into the stem cell a nucleic acid which expresses homeodomain transcription factor Nkx6.1 protein in the stem cell so as to thereby convert the stem cell into the ventral neuron.

This invention also provides a method of diagnosing a motor neuron degenerative disease in a subject which comprises: a) obtaining a nucleic acid sample from the subject; b) sequencing the nucleic acid sample; and c) comparing the nucleic acid sequence of step (b) with a Nkx6.1 nucleic acid sequence from a subject without motor neuron degenerative disease, wherein a difference in the nucleic acid sequence of step (b) from the Nkx6.1 nucleic acid sequence from the subject without motor neuron degenerative disease indicates that the subject has the motor neuron degenerative disease.

This invention provides a method of diagnosing a motor neuron degenerative disease in a subject which comprises: a) obtaining a nucleic acid sample from the subject; b) performing a restriction digest of the nucleic acid sample with a panel of restriction enzymes; c) separating the resulting nucleic acid fragments by size fractionation; d) hybridizing the resulting separated nucleic acid fragments with a nucleic acid probe(s) of at least 15 nucleotide capable of specifically hybridizing with a unique sequence included within the sequence of a nucleic acid molecule encoding a human Nkx6.1 protein, wherein the sequence of the nucleic acid probe is labeled with a detectable marker, and hybridization of the nucleic acid probe(s) with the separated nucleic acid fragments results in labeled probe-fragment bands; e) detecting labeled probe-fragment bands, wherein the labeled probe-fragment bands have a band pattern specific to the nucleic acid of the subject; and f) comparing the band pattern of the detected labeled probe-fragment bands of step (d) with a previously determined control sample, wherein the control sample has a unique band pattern specific to the nucleic acid of a subject having the motor neuron degenerative disease, wherein identity of the band pattern of the detected labeled probe-fragment bands of step (d) to the control sample indicates that the subject has the motor neuron degenerative disease.

This invention provides a method of treating neuronal degeneration in a subject which comprises implanting in diseased neural tissue of the subject a neural stem cell which comprises an isolated nucleic acid molecule which is capable of expressing homeodomain Nkx6.1 protein under conditions such that the stem cell is converted into a motor neuron after implantation, thereby treating neuronal degeneration in the subject.

BRIEF DESCRIPTION OF THE FIGURES

FIGS. 1A-1U Selective changes in homeobox gene expression in ventral progenitor cells in Nkx6.1 mutant embryos.

(FIGS. 1A-1C) Expression of Nkx6.1 in transverse sections of the ventral neural tube of mouse embryos E9.5. (FIG. 1A) Expression of Nkx6.1 is prominent in ventral progenitor cells and persists in some post-mitotic motor neurons at both caudal hindbrain, E10.5, (FIG. 1B) and spinal cord, E12.5, (FIG. 1C) levels. (FIG. 1D, and BE) Summary diagrams showing domains of homeobox gene expression in wild-type mouse embryos (FIG. 1D) and the change in pattern of expression of these genes in Nkx6.1 mutants (FIG. 1E), based on analyses at E10.0-E12.5. (FIGS. 1F-1I) Comparison of the domains of expression of Nkx6.1 (FIGS. 1F, 1J) Dbx2 (FIGS. 1G, 1H, 1K, 1L) and Gsh1 (FIGS. 1I, 1M) in the caudal neural tube of wild-type (FIGS. 1F-1I) and Nkx6.1 mutant (FIGS. 1J-1H) embryos. (FIG. 1J) Horizontal lines, approximate position of dorsoventral boundary of the neural tube; vertical lines, expression of Dbx2 and Gsh1. Expression of Sonic hedgehog, Shh (FIGS. 1N, 1R), Pax7 (FIGS. 1N, 1R), Nkx2.2 (FIGS. 1O, 1S), Pax6 (FIGS. 1P, 1S), Dbx1 (FIGS. 1P, 1T) and Nkx2.9 (FIGS. 1Q, 1U) in wild-type (FIGS. 1N-1Q) or Nkx6.1 mutant (FIGS. 1R-1U) embryos at spinal (FIGS. 1N-1P, 1R-1T) and caudal hindbrain levels (FIGS. 1Q, 1U). Arrowheads, approximate position of the dorsal limit of Nkx6.1 expression. Scale bar shown in J=100 µm (FIGS. 1A-1C); 50 µm (FIGS. 1F-1M) or 60 µm (FIGS. 1N-1U).

The relationship between the domain of Nkx6.1 expression (FIGS. 2A-2C, green) by ventral progenitors and the position of generation of motor neurons and V2 interneurons (FIGS. 2A-2D) in the ventral spinal cord of E10.5 wild-type embryos. (FIG. 2A) Isl1/2 motor neurons; (FIGS. 10Q-10T) Absence, position of Isl1/2 dorsal D2 interneurons. Scale bar shown in I=60 µm (FIGS. 2A-2D); 80 µm (FIGS. 2E-2L); 120 µm (FIGS. 2M-2T).

Depletion of both median motor column (MMC) and lateral motor column (LMC) neurons in Nkx6.1 mutant mice. Expression of Isl1/2 (red) and Lxh3 (green) in E12.5 wilt-type (FIGS. 3A, 3C) and Nkx6.1 mutant (FIGS. 3B, 3D) mice spinal cord at forelimb levels (FIGS. 3E-3J). Motor neuron generation at caudal hindbrain level (FIGS. 3E, 3F) Nkx6.1 expression in progenitor cells and visceral motor neurons in the caudal hindbrain (rhombomere [r] 7/8) of E10.5-E11 wild-type (FIG. 3E) Nkx6.1 mutant (FIG. 3F) mice. HB9 expression in hypoglossal motor neurons in E10.5-E11 wild-type mice (FIG. 3G) and Nkx6.1 mutant (FIG. 3H) mice. Coexpression of Isl1 (green) and Phox2a/b (red) in wild-type (FIG. 3I) or Nkx6.1 mutant (FIG. 3J) mice. (h) hypoglossal motor neurons; (v) visceral vagal motor neurons. Scale bar shown in C=50 µm (FIGS. 3A-3D) or 70 µm (FIGS. 3E-3J).

FIGS. 4A-4L A switch in ventral interneuron fates in Nkx6.1 mutant mice.

Figure 4:
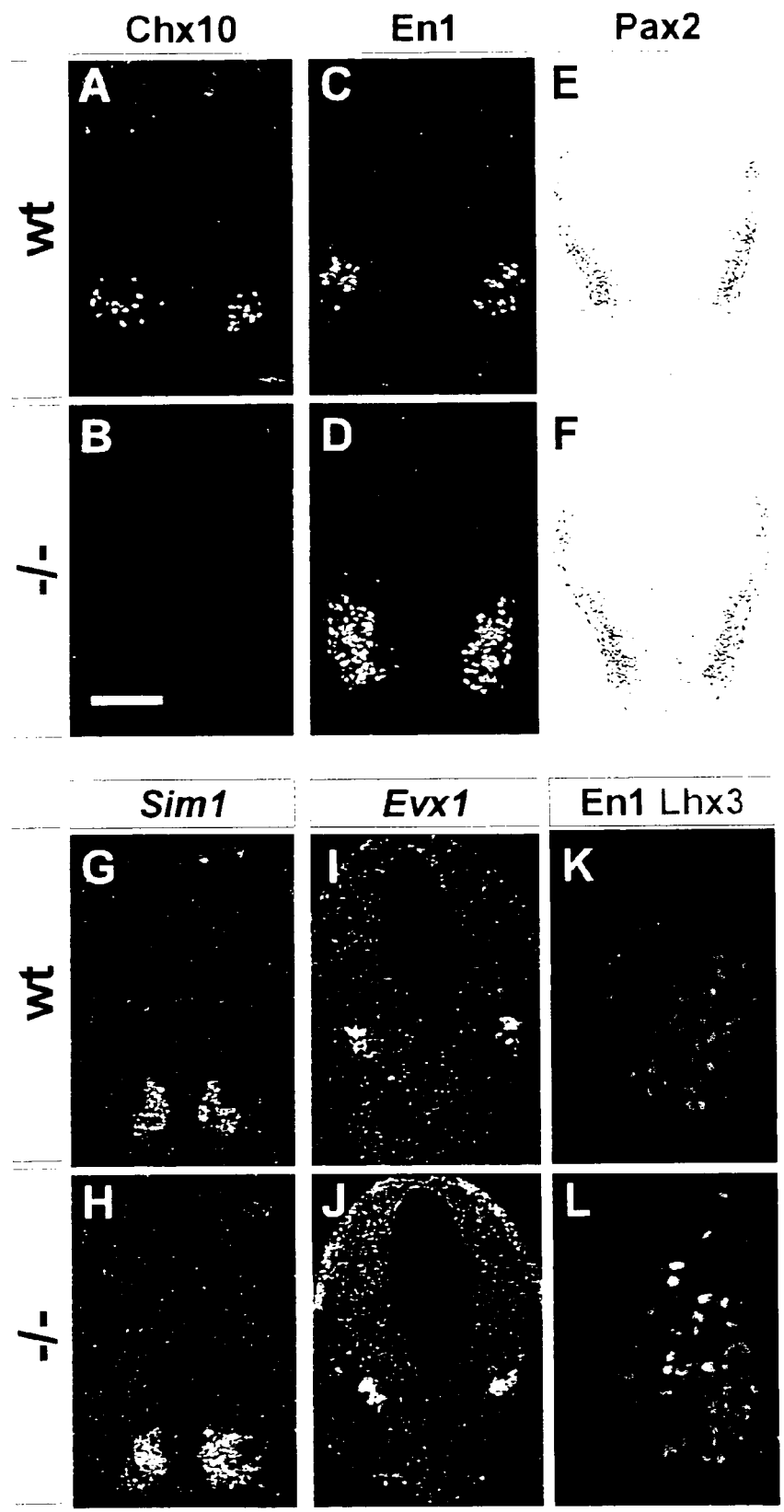

Chx10 expression in V2 neurons at rostral cervical levels of E10.5 wild-type (FIG. 4A) and Nkx6.1 mutant (FIG. 4B) embryos. En1 expression by V1 neurons at rostral cervical levels of wild-type (FIG. 4C) and Nkx6.1 mutant (FIG. 4D) embryos. Pax2 expression in a set of interneurons that includes V1 neurons ((Burrill et al. 1997) at caudal hindbrain levels of wild-type (FIG. 4E) and Nkx6.1 mutant (FIG. 4F) embryos. (FIGS. 4G and 4H) Siml expression by V3 neurons in the cervical spinal cord of wild-type (FIG. 4G) and Nkx6.1 mutant (FIG. 4H) embryos. Evx1 expression by V0 neurons at caudal hindbrain levels of wild-type (FIG. 4I) and Nkx6.1 mutant (FIG. 4J) embryos. En1 (red) and Lhx3 (green) expression by separate cell populations in the ventral spinal cord of E11 wild-type (FIG. 4K) and Nkx6.1 mutant (FIG. 4L) embryos. Scale bar shown in B=60 µm (FIGS. 4A-4D); 75 µm (FIGS. 4E, 4F); 70 µm (FIGS. 4G, 4J, 4H, 4J), 35 µm (FIGS. 4K and 4L).

Figure 5:
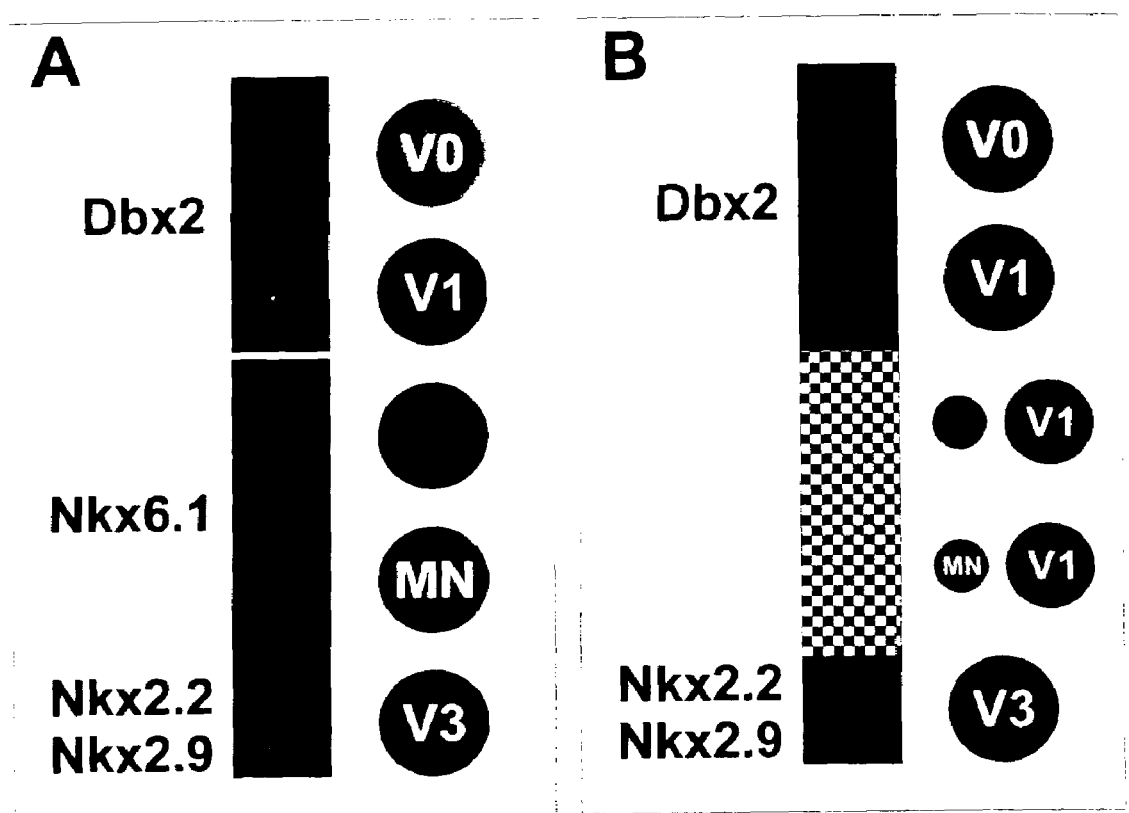

FIGS. 5A-5B Changes in progenitor domain identity and neuronal fate in the spinal cord of Nkx6.1 mutant embryos.

(FIG. 5A). In wild-type mouse embryos, cells in the Nkx6.1 progenitor domain give rise to three classes of ventral neurons: V2 neurons, motor neurons (MN) and V3 neurons. V3 neurons derive from cells in the ventral most region of Nkx6.1 expression that also express Nkx2.2 and Nkx2.9. V1 neurons derive from progenitor cells that express Dbx2 but not Nkx6.1. (FIG. 5B). In Nkx6.1 mutant embryos the domain of Dbx2 expression by progenitor cells expands ventrally, and by embyonic day 12 [E12] occupies the entire dorsoventral extent of the ventral neural tube, excluding the floor plate. Checked area indicates the gradual onset of ventral Dbx2 expression. This ventral shift in Dbx2 expression is associated with a marked decrease in the generation of V2 neurons and motor neurons and a ventral expansion in the domain of generation of V1 neurons. A virtually complete loss of MN and V2 neurons is observed at cervical levels of the spinal cord. The generation of V3 neurons (and cranial visceral motor neurons at hindbrain levels) is unaffected by the loss of Nkx6.1 or by the ectopic expression of Dbx2.

FIG. 6 Human Homeobox Protein Nkx6.1. NCBI Accession No. P78426. (Inoue, H. et al., "Isolation, characterization, and chromosomal mapping of the human Nkx6.1 gene (NKX6a), a new pancreatic islet homeobox gene" Genomics 40(2):367-370, 1997). Amino acid sequence of human homeobox protein Nkx6.1 (SEQ ID NO: 1).

FIG. 7 Human NK Homeobox Protein (Nkx6.1) gene, exon 1. NCBI Accession No. U66797. Segment 1 of 3 (Inoue, H. et al., "Isolation, characterization, and chromosomal mapping of the human Nkx6.1 gene (NKX6a), a new pancreatic islet homeobox gene" Genomics 40(2):367-370, 1997). Nucleic acid sequence encoding human homeobox protein Nkx6.1, bases 1-682 (SEQ ID NO: 2).

FIG. 8 Human NK Homeobox Protein (Nkx6.1) gene, exon 2. NCBI Accession No. U66798. Segment 2 of 3 (Inoue, H. et al., "Isolation, characterization, and chromosomal mapping of the human Nkx6.1 gene (NKX6a), a new pancreatic islet homeobox gene" (Genomics 40(2):367-370, 1997). Nucleic acid sequence encoding human homeobox protein Nkx6.1, bases 1-185 (SEQ ID NO: 3).

FIG. 9 Human NK Homeobox Protein (Nkx6.1) gene, exon 3 and complete cds. NCBI Accession No. U66799. Segment 3 of 3 (Inoue, H. et al., "Isolation, characterization, and chromosomal mapping of the human Nkx6.1 gene (NKX6a), a new pancreatic islet homeobox gene" Genomics 40(2):367-370, 1997). Nucleic acid sequence encoding human homeobox protein Nkx6.1, bases 1-273 (SEQ ID NO: 4). Protein encoded is shown in FIG. 7.

DETAILED DESCRIPTION OF THE INVENTION

This invention provides a method of converting a stem cell into a ventral neuron which comprises introducing into the stem cell a nucleic acid which expresses homeodomain transcription factor Nkx6.1 protein in the stem cell so as to thereby convert the stem cell into the ventral neuron.

In an embodiment of the above-described method of converting a stem cell into a ventral neuron, the nucleic acid introduced into the stem cell incorporates into the chromosomal DNA of the stem cell. In a further embodiment of the method, the nucleic acid is introduced by transfection or transduction. In another further embodiment of the method, the ventral neuron is a motor neuron, a V2 neuron or a V3 neuron.

This invention provides a method of diagnosing a motor neuron degenerative disease in a subject which comprises: a) obtaining a nucleic acid sample from the subject; b) sequencing the nucleic acid sample; and c) comparing the nucleic acid sequence of step (b) with a Nkx6.1 nucleic acid sequence from a subject without motor neuron degenerative disease, wherein a difference in the nucleic acid sequence of step (b) from the Nkx6.1 nucleic acid sequence from the subject without motor neuron degenerative disease indicates that the subject has the motor neuron degenerative disease.

In an embodiment of the above-described method of diagnosing a motor neuron degenerative disease in a subject the motor neuron degenerative disease is amyotrophic lateral sclerosis or spinal muscular atrophy.

This invention provides a method of diagnosing a motor neuron degenerative disease in a subject which comprises: a) obtaining a nucleic acid sample from the subject; b) performing a restriction digest of the nucleic acid sample with a panel of restriction enzymes; c) separating the resulting nucleic acid fragments by size fractionation; d) hybridizing the resulting separated nucleic acid fragments with a nucleic acid probe(s) of at least 15 nucleotide capable of specifically hybridizing with a unique sequence included within the sequence of a nucleic acid molecule encoding a human Nkx6.1 protein, wherein the sequence of the nucleic acid probe is labeled with a detectable marker, and hybridization of the nucleic acid probe(s) with the separated nucleic acid fragments results in labeled probe-fragment bands; e) detecting labeled probe-fragment bands, wherein the labeled probe-fragment bands have a band pattern specific to the nucleic acid of the subject; and f) comparing the band pattern of the detected labeled probe-fragment bands of step (d) with a previously determined control sample, wherein the control sample has a unique band pattern specific to the nucleic acid of a subject having the motor neuron degenerative disease, wherein identity of the band pattern of the detected labeled probe-fragment bands of step (d) to the control sample indicates that the subject has the motor neuron degenerative disease.

In an embodiment of the above-described method of diagnosing a motor neuron degenerative disease in a subject the nucleic acid is DNA. In a further embodiment of the above-described method the nucleic acid is RNA. In another embodiment the size fractionation in step (c) is effected by a polyacrylamide or agarose gel. In another embodiment the detectable marker is radioactive isotope, enzyme, dye, biotin, a fluorescent label or a chemiluminescent label. In yet another embodiment the motor neuron degenerative disease is amyotrophic lateral sclerosis or spinal muscular atrophy.

This invention provides a method of treating neuronal degeneration in a subject which comprises implanting in diseased neural tissue of the subject a neural stem cell which comprises an isolated nucleic acid molecule which is capable of expressing homeodomain Nkx6.1 protein under conditions such that the stem cell is converted into a motor neuron after implantation, thereby treating neuronal degeneration in the subject.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Materials and Methods

Generation of Nkx6.1 Null Mutation

A null mutation in Nkx6.1 was generated by using gene targeting in 129-strain ES cells by excising an 800-bp NotI fragment containing part of exon 1 and replacing it by a PGK-neo cassette (Sander and German, unpubl.) Mutants were born at Mendelian frequency and died soon after birth; they exhibited movements only upon tactile stimulation.

Immunocytochemistry and In Situ Hybridization

Localization of mRNA was performed by in situ hybridization following the method of Schaeren-Wiemers and Gerfin-Moser (1993). The Dbx2 riboprobe comprised the 5' EcoR1 fragment of the mouse cDNA (Pierani et al. 1999). Probes for other cDNAs were cited in the text and used as described therein. Protein expression was localized by indirect fluorescence immunocytochemistry or peroxidase immunocytochemistry (Briscoe et al. 1999; Ericson et al. 1997). Nkx6.1 was detected with a rabbit antiserum (Briscoe et al. 1999). Antisera against Shh, Pax7, Isl1/2, HB9, Lhx3, Chx10, Phox2a/b, En1, and Pax2 have been described (Briscoe et al. 1999; Ericson et al. 1997). Fluorescence detection was carried out using an MRC 1024 Confocal Microscope (BioRad).

RESULTS AND DISCUSSION

Figure 1:
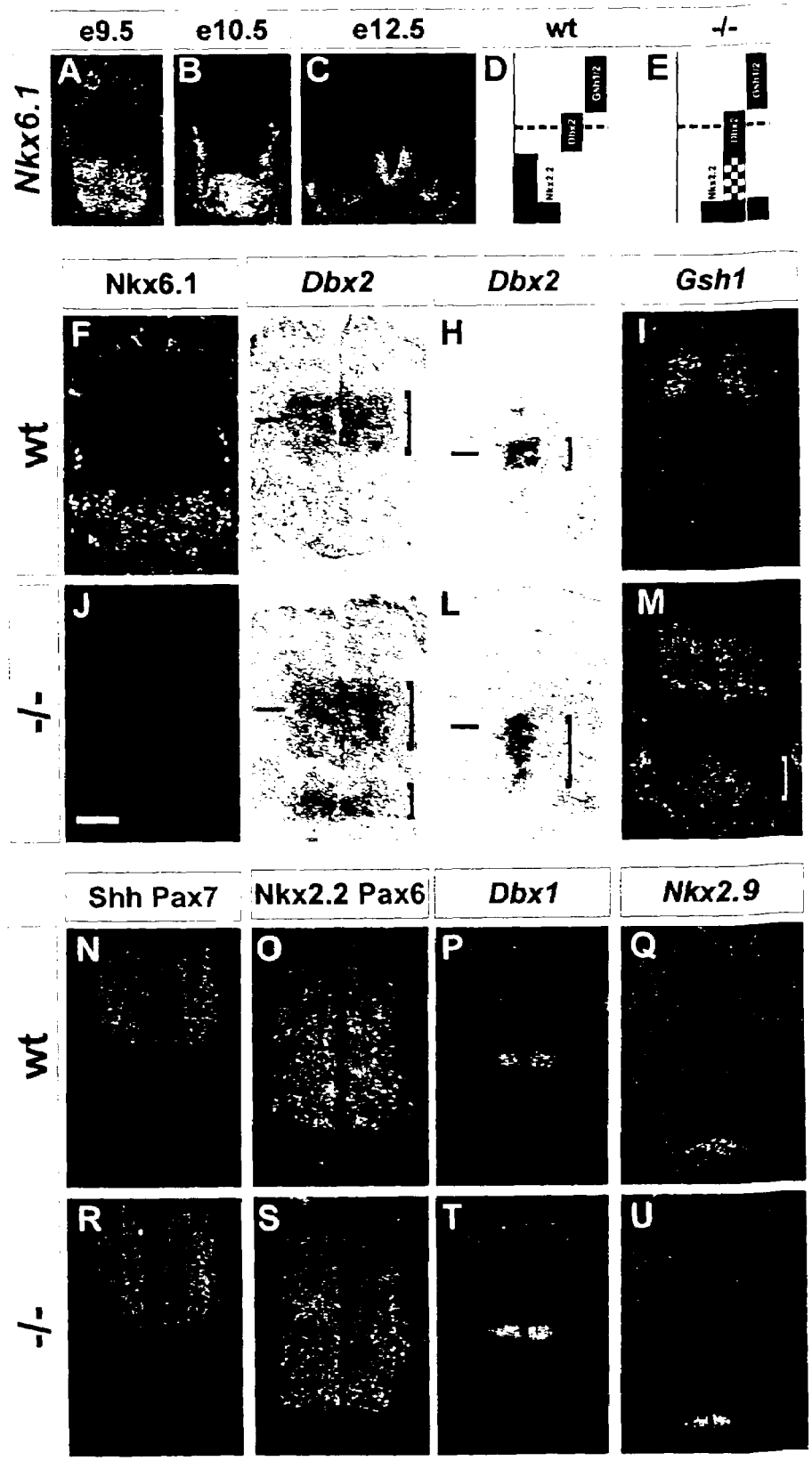
Figure 2:
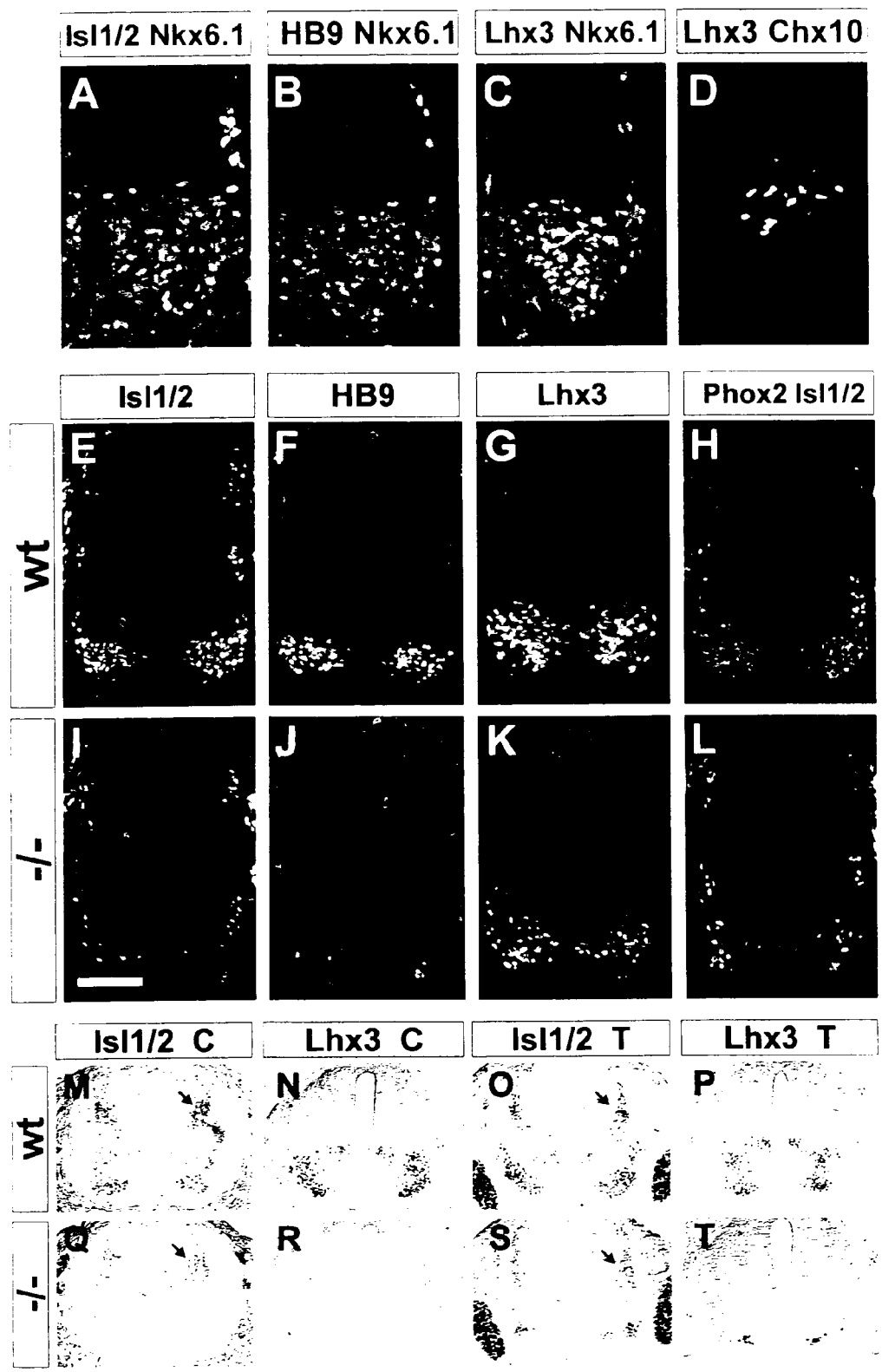
FIGS. 2A-2T. Disruption of motor neuron differentiation in Nkx6.1 mutant embryos.
(FIG. 2B) HB9 motor neurons.
(FIG. 2C) Lhx3 (Lim3) expression (red) by motor neurons, V2 interneurons and their progenitors is confined to the Nkx6.1 progenitor domain.
(FIG. 2D) Chx10 (green) V2 interneurons coexpress Lhx3 (red). Expression of Isl1/2 (FIGS. 2E, 2I), HB9 (FIGS. 2F, 2J), Lhx3 (FIGS. 2G, 2K) and Phox2a/b (FIGS. 2H, 2L) in the ventral spinal cord (FIGS. 2E, 2F, 2G) and caudal hindbrain (FIG. 2H) of E10.5 wild-type (FIGS. 2E-2H) and Nkx6.1 mutant (FIGS. 2I-2L) embryos. Pattern of expression of Isl1/2 and Lhx3 at cervical (FIGS. 2M, 2N, 2Q, 2R) and thoracic (FIGS. 2O, 2P, 2S, 2T) levels of E12.5 wild-type (FIGS. 2M-2P) and Nkx6.1 mutant (FIGS. 2Q-2T) embryos. Arrows, position of Isl1 dorsal D2 interneurons.

To define the role of Nkx6.1 in neural development, we compared patterns of neurogenesis in the embryonic spinal cord and hindbrain of wild-type mice and mice lacking Nkx6.1 (Sander et al. 1998). In wild-type embryos, neural expression of Nkx6.1 is first detected at spinal cord and caudal hindbrain levels at about embryonic day 8.5 (E8.5; Qiu et al. 1998; data not shown), and by E9.5 the gene is expressed throughout the ventral third of the neural tube (FIG. 1A). The expression of Nkx6.1 persists until at least E12.5 (FIGS. 1B, 1C; data not shown). Nkx6.1 expression was also detected in mesodermal cells flanking the ventral spinal cord (FIGS. 1B, 1C). To define more precisely the domain of expression of Nkx6.1, we compared its expressions with that of ten homeobox genes—Pax3, Pax7, Gsh1, Gsh2, Irx3, Pax6, Dbx1, Dbx1, Dbx2 and Nkx2.9—that have been shown to define discrete progenitor cell domains along the dorsoventral axis of the ventral neural tube (Goulding et al. 1991; Valerius et al. 1995; Ericson et al. 1997; Pierani et al. 1999; Briscoe et al. 2000).

This analysis revealed that the dorsal boundary of Nkx6.1 expression is positioned ventral to the boundaries of four genes expressed by dorsal progenitor cells: Pax3, Pax7, Gsh1 and Gsh2 (FIGS. 1I, 1N; and data not shown). Within the ventral neural tube, the dorsal boundary of Nkx6.1 expression is positioned ventral to the domain of Dbx1 expression and close to the ventral boundary of Dbx2 expression (FIGS. 1G, 1H, and 1P). The domain of Pax6 expression extends ventrally into the domain of Nkx6.1 expression (FIG. 1O), whereas the expression of Nkx2.2 and Nkx2.9 overlaps with the ventral-most domain of Nkx6.1 expression (FIGS. 1O, 1Q).

To address the function of Nkx6.1 in neural development, we analyzed progenitor cell identity and the pattern of neuronal differentiation in Nkx6.1 null mutant mice (Sander et al. 1998). We detected a striking change in the profile of expression of three homeobox genes, Dbx2, Gsh1 and Gsh2, in Nkx6.1 mutants. The domains of expression of Dbx2, Gsh1 and Gsh2 each expanded into the ventral neural tube (FIGS. 1K-1M; data not shown). At E10.5, Dbx2 was expressed at high levels by progenitor cells adjacent to the floor plate, but at this stage ectopic Dbx2 expression was detected only at low levels in regions of the neural tube that generate motor neurons (FIG. 1K). By E12.5, however, the ectopic ventral expression of Dbx2 had become more uniform, and now clearly included the region of motor neuron and V2 neuron generation (FIG. 1L). Similarly, in Nkx6.1 mutants, both Gsh1 and Gsh2 were ectopically expressed in a ventral domain of the neural tube, and also in adjacent paraxial mesodermal cells (FIG. 1M; data not shown).

The ventral limit of Pax6 expression was unaltered in Nkx6.1 mutants, although the most ventrally located cells within this progenitor domain expressed a higher level of Pax6 protein than those in wild-type embryos (FIGS. 1O, 1S). We detected no change in the patterns of expression of Pax3, Pax7, Dbx1, Irx3, Nkx2.2, or Nkx2.9 in Nkx6.1 mutant embryos (FIGS. 1R-1U; data not shown). Importantly, the level of Shh expression by floor plate cells was unaltered in Nkx6.1 mutants (FIGS. 1N and 1R). Thus, the loss of Nkx6.1 function deregulates the patterns of expression of a selected subset of homeobox genes in ventral progenitor cells, without an obvious effect on Shh levels (FIGS. 1D, 1E). The role of Shh in excluding Dbx2 from the most ventral region of the neural tube (Pierani et al. 1999) appears therefore to be mediated through the induction of Nkx6.1 expression. Consistent with this view, ectopic expression of Nkx6.1 represses Dbx2 expression in chick neural tube (Briscoe et al. 2000). The detection of sites of ectopic Gsh1/2 expression in the paraxial mesoderm as well as the ventral neural tube, both sites of Nkx6.1 expression, suggests that Nkx6.1 has a general role in restricting Gsh1/2 expression. The signals that promote ventral Gsh1/2 expression in Nkx6.1 mutants remain unclear, but could involve factors other than Shh that are secreted by the notochord (Hebrok et al. 1998).

The domain of expression of Nkx6.1 within the ventral neural tube of wild-type embryos encompasses the progenitors of three main neuronal classes: V2 interneurons, motor neurons and V3 interneurons (Goulding et al. 1991; Ericson et al. 1997; Qiu et al. 1998; Briscoe et al. 1999, 2000; Pierani et al. 1999; FIGS. 2A-2D). We examined whether the generation of any of these neuronal classes is impaired in Nkx6.1 mutants, focusing first on the generation of motor neurons. In Nkx6.1 mutant embryos there was a marked reduction in the number of spinal motor neurons, as assessed by expression of the homeodomain proteins Lhx3, Isl1/2 and HB9 (Arber et al. 1999; Tsuchida et al. 1994; FIGS. 2E-2L), and by expression of the gene encoding the transmitter synthetic enzyme choline acetyltransferase (data not shown). In addition, few if any axons were observed to emerge from the ventral spinal cord (data not shown). The incidence of motor neuron loss, however, varied along the rostrocaudal axis of the spinal cord. Few if any motor neurons were detected at caudal cervical and upper thoracic levels of Nkx6.1 mutants analyzed at E11-E12.5 (FIGS. 2M, 2N, 2Q, 2R), whereas motor neuron number was reduced only by 50%-75% at more caudal levels (FIGS. 2O, 2P, 2S, 2T; data not shown). At all axial levels, the initial reduction in motor neuron number persisted at both E12.5 and p0 (FIGS. 2M-2T; data not shown), indicating that the loss of Nkx6.1 activity does not simply delay motor neuron generation. Moreover, we detected no increase in the incidence of TUNEL[+] cells in Nkx6.1 mutants (data not shown), providing evidence that the depletion of motor neurons does not result solely from apoptotic death.

Figure 3:
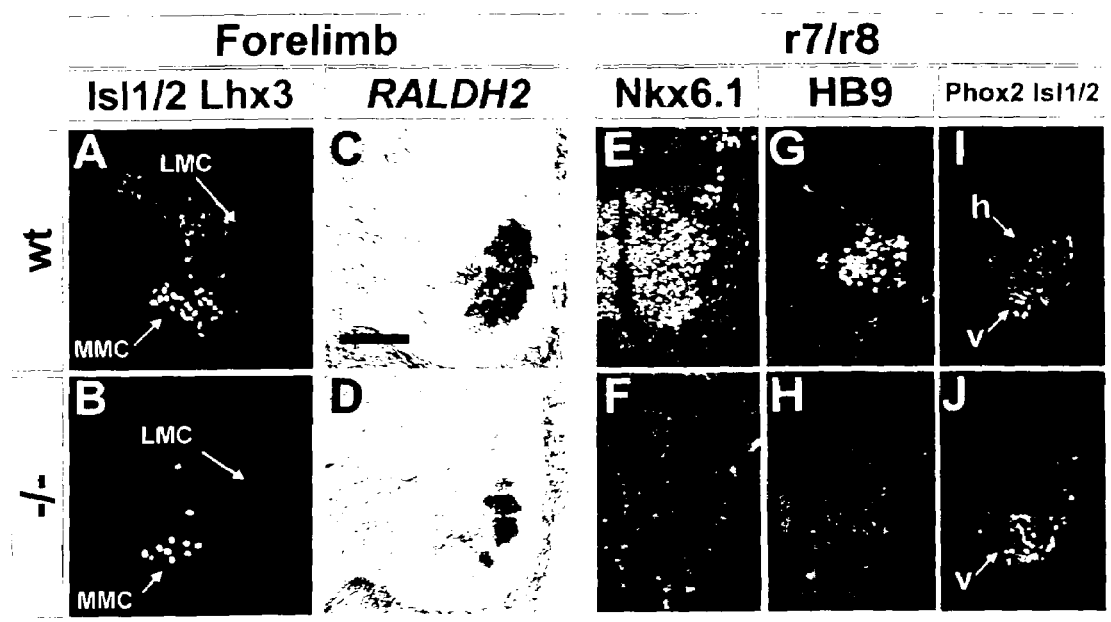
FIGS. 3A-3J Motor neuron subtype differentiation in Nkx6.1 mutant mice.

The persistence of some spinal motor neurons in Nkx6.1 mutants raised the possibility that the generation of particular subclasses of motor neurons is selectively impaired. To address this issue, we monitored the expression of markers of distinct subtypes of motor neurons at both spinal and hindbrain levels of Nkx6.1 mutant embryos. At spinal levels, the extent of the reduction in the generation of motor neurons that populate the median (MMC) and lateral (LMC) motor columns was similar in Nkx6.1 mutants, as assessed by the number of motor neurons that coexpressed Isl1/2 and Lhx3 (defining MMC neurons, FIGS. 3A, 3B) and by the expression of Raldh2 (defining LMC neurons, Sockanathan and Jessell 1998; Arber et al. 1999; FIGS. 3C, 3D). In addition, the generation of autonomic visceral motor neurons was reduced to an extent similar to that of somatic motor neurons at thoracic levels of the spinal cord of E12.5 embryos (data not shown). Thus, the loss of Nkx6.1 activity depletes the major subclasses of spinal motor neurons to a similar extent.

At hindbrain levels, Nkx6.1 is expressed by the progenitors of both somatic and visceral motor neurons (FIGS. 3E, 3F; data not shown). We therefore examined whether the loss of Nkx6.1 might selectively affect subsets of cranial motor neurons. We detected a virtually complete loss in the generation of hypoglossal and abducens somatic motor neurons in Nkx6.1 mutants, as assessed by the absence of dorsally generated HB9[+] motor neurons (FIGS. 3G, 3H; data not shown, Arber et al. 1999; Briscoe et al. 1999). In contrast, there was no change in the initial generation of any of the cranial visceral motor neuron populations, assessed by coexpression of Isl1 and Phox2a (Briscoe et al. 1999; Pattyn et al. 1997) within ventrally generated motor neurons (FIGS. 3I, 3J; data not shown). Moreover, at rostral cervical levels, the generation of spinal accessory motor neurons (Ericson et al. 1997) was also preserved in Nkx6.1 mutants (data not shown). Thus, in the hindbrain the loss of Nkx6.1 activity selectively eliminates the generation of somatic motor neurons, while leaving visceral motor neurons intact. Cranial visceral motor neurons, unlike spinal visceral motor neurons, derive from progenitors that express the related Nkx genes Nkx2.2 and Nkx2.9 (Briscoe et al. 1999). The preservation of cranial visceral motor neurons in Nkx6.1 mutant embryos may therefore reflect the dominant activities of Nkx2.2 and Nkx2.9 within these progenitor cells.

We next examined whether the generation of ventral interneurons is affected by the loss of Nkx6.1 activity. V2 and V3 interneurons are defined, respectively, by expression of Chx10 and Sim1 (Arber et al. 1999; Briscoe et al. 1999; FIGS. 4A, 4G). A severe loss of Chx10 V2 neurons was detected in Nkx6.1 mutants at spinal cord levels (FIG. 4B), although at hindbrain levels of Nkx6.1 mutants ~50% of V2 neurons persisted (data not shown). In contrast, there was no change in the generation of Sim1 V3 interneurons at any axial level of Nkx6.1 mutants (FIG. 4H). Thus, the elimination of Nkx6.1 activity affects the generation of only one of the two major classes of ventral interneurons that derive from the Nkx6.1 progenitor cell domain.

Evx1+, Pax2+ V1 interneurons derive from progenitor cells located dorsal to the Nkx6.1 progenitor domain, (FIG. 4B) within a domain that expresses Dbx2, but not Dbx1 (Burrill et al. 1997; Matise and Joyner 1997; Pierani et al. 1999). Because Dbx2 expression undergoes a marked ventral expansion in Nkx6.1 mutants, we examined whether there might be a corresponding expansion in the domain of generation of V1 neurons. In Nkx6.1 mutants, the region that normally gives rise to V2 neurons and motor neurons now also generated V1 neurons, as assessed by the ventral shift in expression of the En1 and Pax2 homeodomain proteins (FIGS. 4B, 4C, 4E, 4F). Consistent with this, there was a two- to threefold increase in the total number of V1 neurons generated in Nkx6.1 mutants (FIGS. 4C, 4D). In contrast, the domain of generation of Evx1/2 V0 neurons, which derive from the Dbx1 progenitor domain (Pierani et al. 1999), was unchanged in Nkx6.1 mutants (FIGS. 4I, 4J). Thus, the ventral expansion in Dbx2 expression is accompanied by a selective switch in interneuronal fates, from V2 neurons to V1 neurons. In addition, we observed that some neurons within the ventral spinal cord of Nkx6.1 mutants coexpressed the V1 marker En1 and the V2 marker Lhx3 (FIGS. 4K, 4L). The coexpression of these markers is rarely if ever observed in single neurons in wild type embryos (Ericson et al. 1996). Thus, within individual neurons in Nkx6.1 mutants, the ectopic program of V1 neurogenesis appears to be initiated in parallel with a residual, albeit transient, program of V2 neuron generation. This result complements observations in Hb9 mutant mice, in which the programs of V2 neuron and motor neuron generation coincide transiently within individual neurons (Arber et al. 1999; Thaler et al. 1999).

Taken together, the findings herein reveal an essential role for the Nkx6.1 homeobox gene in the specification of regional pattern and neuronal fate in the ventral half of the mammalian CNS. Within the broad ventral domain within which Nkx6.1 is expressed (FIG. 5A), its activity is required to promote motor neuron and V2 interneuron generation and to restrict the generation of V1 interneurons (FIG. 5B). It is likely that the loss of motor neurons and V2 neurons is a direct consequence of the loss of Nkx6.1 activity, as the depletion of these two neuronal subtypes is evident at stages when only low levels of Dbx2 are expressed ectopically in most regions of the ventral neural tube. Nonetheless, it can not be excluded that low levels of ectopic ventral Dbx2 expression could contribute to the block in motor neuron generation. Consistent with this view, the ectopic expression of Nkx6.1 is able to induce both motor neurons and V2 neurons in chick neural tube (Briscoe et al. 2000). V3 interneurons and cranial visceral motor neurons derive from a set of Nkx6.1 progenitors that also express Nkx2.2 and Nkx2.9 (Briscoe et al. 1999, FIG. 5A). The generation of these two neuronal subtypes is unaffected by the loss of Nkx6.1 activity, suggesting that the actions of Nkx2.2 and Nkx2.9 dominate over that of Nkx6.1 within these progenitors. The persistence of some spinal motor neurons and V2 neurons in Nkx6.1 mutants could reflect the existence of a functional homologue within the caudal neural tube.

The role of Nkx6.1 revealed in these studies, taken together with previous findings, suggests a model in which the spatially restricted expression of Nkx genes within the ventral neural tube (FIG. 5) has a pivotal role in defining the identity of ventral cell types induced in response to graded Shh signaling. Strikingly, in *Drosophila*, the Nkx gene NK2 has been shown to have an equivalent role in specifying neuronal fates in the ventral nerve cord (Chu et al. 1998; McDonald et al. 1998). Moreover, the ability of Nkx6.1 to function as a repressor of the dorsally expressed Gsh1/2 homeobox genes parallels the ability of *Drosophila* NK2 to repress Ind, a Gsh1/2-like homeobox gene (Weiss et al. 1998). Thus, the evolutionary origin of regional pattern along the dorsoventral axis of the central nervous system may predate the divergence of invertebrate and vertebrate organisms.

REFERENCES

1. S. A. Anderson, D. D. Eisenstat, L. Shi, J. L. Rubenstein, *Science* 278:474-476 (1997).
2. S. Arber, B. Han, M. Mendelsohn, M. Smith, T. M. Jessell, S. Sockanathan, *Neuron* 23:659-674 (1999).
3. J. Briscoe, et al., *Nature* 398:622-627 (1999).
4. J. Briscoe et al., *Cell* 101:435-445 (2000).
5. J. D. Burrill, L. Moran, M. D. Goulding, H. Saueressig, *Development* 124:4493-4503 (1997).
6. H. Chu; C. Parras; K. White; F. Jimenez, *Genes & Dev.* 12:3613-3624 (1998).
7. J. Ericson, et al., *Cold Spring Harb. Symp. Quant. Biol.* 62:451-466 (1997a).
8. J. Ericson et al., *Cell* 87:661-673 (1996).
9. J. Ericson, et al., *Cell.* 90:169-180 (1997b).
10. M. D. Goulding et al., *EMBO J.* 10:1135-47 (1991).
11. M. Hammerschmidt, A. Brook, A. P. McMahon *Trends Genet.* 13:14-21 (1997)
12. M. Hebrok, S. K. Kim, D. A. Melton, *Genes & Dev.* 12: 1705-1713 (1998).
13. A. Lumsden, R., and Krumlauf, R. *Science* 274: 1109-1115 (1996).
14. M. P. Matise, A. L. Joyner, *J. Neurosci.* 17:7805-7816 (1998).
15. J. A. McDonald, S. Holbrook, T. Isshiki, J. Weiss, C. Q. Doe, D. M. Mellerick. *Genes & Dev.* 12:3603-3612 (1998).
16. O. Pabst, H. Herbrand, H. H. Arnold, *Mech. Dev.* 73: 85-93 (1998).
17. A. Pattyn, X. Morin, H. Cremer, C. Goridis, J. F. Brunet, *Development* 124:4065-4075 (1997).
18. A. Pierani, S. Brenner-Morton, C. Chiang, T. M. Jessell, *Cell* 97:903-915 (1999).
19. M. Qiu, K. Shimamura, L. Sussel, S. Chen, J. L. Rubenstein, *Mech. Dev.* 72:77-88 (1998).
20. J. L. Rubenstein and Beachy, P. A. *Curr. Opin. Neurobiol.* 8:18-26 (1998).
21. J. L. Rubenstein et al., *Annu Rev Neurosci.* 21:445-477 (1998).
22. Sander, M. et al. *Keystone symposium on vertebrate development*. Steamboat Springs, Colo. (1998).
23. Schaeren-Wiemers, N. and Gerlin-Moser, A. *Histochemistry* 100:431-440 (1993).
24. Sockanathan, S. and Jessell, T. M. *Cell* 94:503-514 (1998).
25. L. Sussel, O. Marin, S. Kimura, J. L. Rubenstein, *Development* 126:3359-3370 (1999).
26. Y. Tanabe, and T. M. Jessell, *Science* 274:1115-23 (1996).
27. J. Thaler et al., *Neuron* 23:675-687 (1999).
28. T. Tsuchida, et al., *Cell* 79:957-970 (1994).
29. M. T. Valerius, H. Li, J. L. Stock, M. Weinstein, S. Kaur, G. Singh, S. S. Potter, *Dev. Dyn.* 203:337-51 (1995).
30. J. B. Weiss, T. Von Ohlen, D. M. Mellerick, G. Dressler, C. Q. Doe, M. P. Scott, *Genes & Dev.* 12:3591-3602 (1998).

What is claimed is:

1. A method of converting a neural stem cell into a V2 interneuron which comprises introducing into the neural stem cell, ex vivo, a retroviral vector comprising a nucleic acid which encodes homeodomain transcription factor Nkx6.1 protein, wherein the encoded protein is expressed in the neural stem cell so as to thereby convert the neural stem cell into the V2 interneuron.

2. The method of claim 1, wherein the nucleic acid introduced into the neural stem cell integrates into the chromosomal DNA of the neural stem cell.

* * * * *

SEQUENCE LISTING

<160> NUMBER OF SEQ ID NOS: 4

<210> SEQ ID NO 1
<211> LENGTH: 367
<212> TYPE: PRT
<213> ORGANISM: Human

<400> SEQUENCE: 1

```
Met Leu Ala Val Gly Ala Met Glu Gly Thr Arg Gln Ser Ala Phe Leu
1               5                   10                  15

Leu Ser Ser Pro Pro Leu Ala Ala Leu His Ser Met Ala Glu Met Lys
            20                  25                  30

Thr Pro Leu Tyr Pro Ala Ala Tyr Pro Pro Leu Pro Ala Gly Pro Pro
        35                  40                  45

Ser Ser Ser Ser Ser Ser Ser Ser Ser Ser Pro Ser Pro Pro Leu
    50                  55                  60

Gly Thr His Asn Pro Gly Gly Leu Lys Pro Pro Ala Thr Gly Gly Leu
65                  70                  75                  80

Ser Ser Leu Gly Ser Pro Pro Gln Gln Leu Ser Ala Ala Thr Pro His
                85                  90                  95

Gly Ile Asn Asn Ile Leu Ser Arg Pro Ser Met Pro Val Ala Ser Gly
                100                 105                 110

Ala Ala Leu Pro Ser Ala Ser Pro Ser Gly Ser Ser Ser Ser Ser Ser
            115                 120                 125

Ser Ser Ala Ser Ala Ser Ser Ala Ser Ala Ala Ala Ala Ala Ala Ala
    130                 135                 140

Ala Ala Ala Ala Ala Ala Ser Pro Ala Gly Leu Leu Ala Gly Leu
145                 150                 155                 160

Pro Arg Phe Ser Ser Leu Ser Pro Pro Pro Pro Gly Leu Tyr
                165                 170                 175

Phe Ser Pro Ser Ala Ala Ala Val Ala Ala Val Gly Arg Tyr Pro Lys
                180                 185                 190

Pro Leu Ala Glu Leu Pro Gly Arg Thr Pro Ile Phe Trp Pro Gly Val
                195                 200                 205

Met Gln Ser Pro Pro Trp Arg Asp Ala Arg Leu Ala Cys Thr Pro His
210                 215                 220

Gln Gly Ser Ile Leu Leu Asp Lys Asp Gly Lys Arg Lys His Thr Arg
225                 230                 235                 240

Pro Thr Phe Ser Gly Gln Gln Ile Phe Ala Leu Glu Lys Thr Phe Glu
                245                 250                 255

Gln Thr Lys Tyr Leu Ala Gly Pro Glu Arg Ala Arg Leu Ala Tyr Ser
            260                 265                 270

Leu Gly Met Thr Glu Ser Gln Val Lys Val Trp Phe Gln Asn Arg Arg
        275                 280                 285

Thr Lys Trp Arg Lys Lys His Ala Ala Glu Met Ala Thr Ala Lys Lys
    290                 295                 300

Lys Gln Asp Ser Glu Thr Glu Arg Leu Lys Gly Ala Ser Glu Asn Glu
305                 310                 315                 320

Glu Glu Asp Asp Asp Tyr Asn Lys Pro Leu Asp Pro Asn Ser Asp Asp
                325                 330                 335

Glu Lys Ile Thr Gln Leu Leu Lys Lys His Lys Ser Ser Ser Gly Gly
            340                 345                 350

Gly Gly Gly Leu Leu Leu His Ala Ser Glu Pro Glu Ser Ser Ser
```

-continued

```
                     355                 360                 365

<210> SEQ ID NO 2
<211> LENGTH: 682
<212> TYPE: DNA
<213> ORGANISM: Human

<400> SEQUENCE: 2
cgtgggatgt tagcggtggg ggcaatggag ggcacccggc agagcgcatt cctgctcagc      60
agccctcccc tggccgccct gcacagcatg gccgagatga agaccccgct gtaccctgcc     120
gcgtatcccc cgctgcctgc cggcccccccc tcctcctcgt cctcgtcgtc gtcctcctcg     180
tcgccctccc cgcctctggg cacccacaac ccaggcggcc tgaagccccc ggccacgggg     240
gggctctcat ccctcggcag ccccccgcag cagctctcgg ccgccacccc acacggcatc     300
aacaatatcc tgagccggcc ctccatgccc gtggcctcgg gggccgccct gccctccgcc     360
tcgccctccg gttcctcctc ctcctcttcc tcgtccgcct ctgcctcctc cgcctctgcc     420
gccgccgcgg ctgctgccgc ggccgcagcc gccgcctcat ccccggcggg gctgctggcc     480
ggactgccac gctttagcag cctgagcccg ccgccgccgc cgcccgggct ctacttcagc     540
cccagcgccg cggccgtggc cgccgtgggc cggtacccca agccgctggc tgagctgcct     600
ggccggacgc ccatcttctg gcccggagtg atgcagagcc cgccctggag ggacgcacgc     660
ctggcctgta cccctcgtga gt                                              682

<210> SEQ ID NO 3
<211> LENGTH: 185
<212> TYPE: DNA
<213> ORGANISM: Human

<400> SEQUENCE: 3
tcacagatca aggatccatt ttgttggaca aagacgggaa gagaaaacac acgagaccca      60
ctttttccgg acagcagatc ttcgccctgg agaagacttt cgaacaaaca aaatacttgg     120
cggggcccga gagggctcgt ttggcctatt cgttggggat gacagagagt caggtcaagg     180
tgagt                                                                 185

<210> SEQ ID NO 4
<211> LENGTH: 273
<212> TYPE: DNA
<213> ORGANISM: Human

<400> SEQUENCE: 4
cctcaggtct ggttccagaa ccgccggacc aagtggagga agaagcacgc tgccgagatg      60
gccacggcca agaagaagca ggactcggag acagagcgcc tcaaggggc ctcggagaac     120 gaggaagagg acgacgacta caataagcct ctggatccca actcggacga cgagaaaatc     180
acgcagctgt tgaagaagca caagtccagc agcggcggcg gcggcggcct cctactgcac     240
gcgtccgagc cggagagctc atcctgaacg ccg                                  273
```